(12) United States Patent
Matthews et al.

(10) Patent No.: US 8,722,607 B2
(45) Date of Patent: May 13, 2014

(54) METHODS AND COMPOSITIONS FOR ELIMINATING ALLERGENS AND ALLERGEN-PRODUCING ORGANISMS

(75) Inventors: Michael A. Matthews, Columbia, SC (US); Jian Zhang, Sunnyvale, CA (US); Allan M. Quick, Lexington, SC (US)

(73) Assignee: University of South Carolina, Columbia, SC (US)

( * ) Notice: Subject to any disclaimer, the term of this patent is extended or adjusted under 35 U.S.C. 154(b) by 377 days.

(21) Appl. No.: 13/070,845

(22) Filed: Mar. 24, 2011

(65) Prior Publication Data

US 2011/0232683 A1     Sep. 29, 2011

Related U.S. Application Data

(60) Provisional application No. 61/340,897, filed on Mar. 24, 2010, provisional application No. 61/398,812, filed on Jul. 1, 2010.

(51) Int. Cl.
| | | |
|---|---|---|
| *C11D 7/60* | (2006.01) | |
| *C11D 3/39* | (2006.01) | |
| *C11D 3/48* | (2006.01) | |
| *B08B 7/00* | (2006.01) | |

(52) U.S. Cl.
CPC ............. *C11D 3/3947* (2013.01); *C11D 3/48* (2013.01); *B08B 7/0021* (2013.01)
USPC ........................................ 510/278; 134/26

(58) Field of Classification Search
CPC ....... C11D 3/3947; C11D 3/48; B08B 7/0021
USPC .............................................. 510/278; 134/26
See application file for complete search history.

(56) References Cited

U.S. PATENT DOCUMENTS

| | | |
|---|---|---|
| 6,235,701 B1 | 5/2001 | Elsbernd |
| 6,491,231 B1 | 12/2002 | Eliasson et al. |
| 6,962,714 B2 * | 11/2005 | Hei et al. .................. 424/405 |
| 6,966,144 B2 | 11/2005 | Eliasson et al. |
| 7,293,570 B2 | 11/2007 | Jackson |

(Continued)

FOREIGN PATENT DOCUMENTS

WO          WO 03090805          11/2003

OTHER PUBLICATIONS

An et al., "Effects of sterilization on implant mechanical property and biocompatibility—A concise review". International Journal of Artificial Organs 2005, 28, 1126-1137.

(Continued)

*Primary Examiner* — Gregory Webb
(74) *Attorney, Agent, or Firm* — Dority & Manning, P.A.

(57) ABSTRACT

Methods are provided for making a treatment composition by loading active components into a high pressure vessel and pressurizing the high pressure vessel with carbon dioxide to reach a pressure within the high pressure vessel of about 400 pounds per square inch to about 1,070 pounds per square inch. The active components can include a protein denaturant and a surfactant, and optionally an acaricide. In one particular embodiment, this method can be used to clean a substrate, by loading the substrate into the high pressure vessel prior to pressurizing with carbon dioxide. Methods are also provided for treating a substrate to clean it from dust mites by delivering dry ice particles to the substrate, and vacuuming the substrate. Treatment compositions are also generally provided.

7 Claims, 5 Drawing Sheets

(56) References Cited

U.S. PATENT DOCUMENTS

| | | | |
|---|---|---|---|
| 2004/0033269 | A1 | 2/2004 | Hei et al. |
| 2005/0054702 | A1 | 3/2005 | Dunn et al. |
| 2005/0156065 | A1 | 7/2005 | Eliasson |
| 2005/0227897 | A1 | 10/2005 | Nelson et al. |
| 2005/0288204 | A1* | 12/2005 | Matts et al. .................. 510/375 |
| 2011/0236256 | A1 | 9/2011 | Matthews et al. |
| 2012/0035089 | A1 | 2/2012 | Matthews et al. |
| 2012/0066841 | A1 | 3/2012 | Matthews et al. |

OTHER PUBLICATIONS

Ballestra et al., "Inactivation of *Escherichia coli* by carbon dioxide under pressure". Journal of Food Science 1996, 61, 829-831, 836.
Ballestra et al., "Influence of pressurized carbon dioxide on the thermal inactivation of bacterial and fungal spores". Lebensmittel-Wissenschaft und-Technologie 1998, 31, 84-88.
Bell et al. "Biomedical membranes from hydrogels and interpolymer complexes". Advances in Polymer Science 1995, 122, 125-175.
Cappuccino et al. Microbiology A Laboratory Manual 2001, 123.
Collier et al. "Comparison of cross-linked polyethylene materials for orthopaedic applications". Clinical orthopaedics and related research 2003, 414, 289-304.
Costa et al. "Invivo UHMWPE biodegradation of retrieved prosthesis". Biomaterials 1998, 19, 1371-1385.
Debs-Louka et al. "Effect of compressed carbon dioxide on microbial cell viability". Applied and Environmental Microbiology 1999, 65, 626-631.
Dillow et al. "Bacterial inactivation by using near- and supercritical carbon dioxide". Proceedings of the National Academy of Sciences of the United States of America 1999, 96, 10344-10348.
Elvassore et al. "Micro-organisms inactivation by supercritical CO2 in a semi-continuous process". In: Perrut M, Reverchon E, editors; Dec. 6-8, 2000; Antibes (France). p. 773-778.
Enomoto et al. "Inactivation of food microorganisms by high-pressure carbon dioxide treatment with or without explosive decompression". Bioscience Biotechnology and Biochemistry 1997, 61, 1133-1137.
Erkmen, O. "Antimicrobial effect of pressurized carbon dioxide on *Staphylococcus aureus* in broth and milk". Food Science & Technology (London) 1997, 30, 826-829.
Erkmen, O. "Effect of carbon dioxide pressure on *Listeria monocytogenes* in physiological saline and foods". Food Microbiology 2000, 17, 589-596.
Erkmen, O. "Inactivation of *Salmonella typhimurium* by high pressure carbon dioxide". Food Microbiology 2000, 17, 225-232.
Erkmen, O. "Effects of high-pressure carbon dioxide on *Escherichia coli* in nutrient broth and milk". International Journal of Food Microbiology 2001, 65, 131-135.
Erkmen, O. "Kinetic analysis of *Listeria monocytogenes* inactivation by high pressure carbon dioxide". Journal of Food Engineering 2001, 42, 7-10.
Farewell et al. "Effect of temperature on in vivo protein synthetic capacity in *Escherichia coli*". Journal of Bacteriology 1998, 180, 4704-4710.
Galas et al. "Humidity-conditioned gravimetric method to measure the water content of hydrogel contact lens materials". Optometry and Vision Science: Official Publication of the American Academy of Optometry 1993, 70, 577-586.
Ghandehari et al. "In vitro degradation of pH-sensitive hydrogels containing aromatic azo bonds". Biomaterials 1997, 18, 861-872.
Hong et al. "Non-thermal inactivation of *Lactobacillus plantarum* as influenced by pressure and temperature of pressurized carbon dioxide". International Journal of Food Science and Technology 1999, 34, 125-130.
Ishikawa et al. "Inactivation of *Bacillus* spores by the supercritical carbon dioxide micro-bubble method". Bioscience, Biotechnology, and Biochemistry 1997, 61, 1022-1023.
Jimenez et al. Evaluation of CO2- Based Cold Sterilization of a Model Hydrogel, Biotech Bioeng., 101(6), 1344-1352, 2008.

Kamihira et al. "Sterilization of microorganisms with supercritical carbon dioxide". Agricultural and Biological Chemistry 1987, 51, 407-12.
Kishida et al. "Hydrogels for biomedical and pharmaceutical applications". Polymeric Biomaterials (2nd Edition) 2002, 133-145.
Koros et al. "High-pressure sorption of carbon dioxide in solvent-cast poly(methyl methacrylate) and poly(ethyl methacrylate) films". Journal of Applied Polymer Science 1981, 26, 159-170.
Lee et al. "Synthesis and characteristics of interpenetrating polymer network hydrogel composed of chitosan and poly(acrylic acid)". Journal of Applied Polymer Science 1999, 73, 113-120.
Lopatin et al. "Structure and relaxation properties of medical-purposed polyacrylamide gels". Journal of Applied Polymer Science 2005, 96, 1043-1058.
McHugh et al. "Supercritical Fluid Extraction". Newton, MA: Butterworth-Heinemann. 1994, 1-16 p.
Park GB. "Burn wound coverings—a review". Biomaterials, Medical Devices, and Artificial Organs 1978, 6, 1-35.
Ruel-Gariepy et al. "Thermosensitive chitosan-based hydrogel containing liposomes for the delivery of hydrophilic molecules". Journal of Controlled Release 2002, 82, 373-383.
Sawan et al. "Evaluation of the Interactions Between Supercritical Carbon Dioxide and Polymeric Materials". Lowell, MA: Los Alamos National Laboratory. 1995, 7-32 p.
Schmidt et al. "Disinfection of textile materials contaminated with *E. coli* in liquid carbon dioxide". Journal of Cleaner Production 2005, 13, 881.
Span et al. "A new equation of state for carbon dioxide covering the fluid region from the triple-point temperature to 1100 K at pressures up to 800 MPa". Journal of Physical and Chemical Reference Data 1996, 25, 1509-1596.
Spilimbergo et al. "Non-thermal bacterial inactivation with dense CO2". Biotechnology and Bioengineering 2003, 84, 627-638.
Stockar, U. "Effect of a near-critical and supercritical fluid on the viability ratio of microbial cells". Progress in Biotechnology 1992, 8, 407-416.
White et al. "Effective terminal sterilization using supercritical carbon dioxide". Journal of Biotechnology 2006, 123, 504-515.
Wu et al. "Influence of the COOH and COONa groups and crosslink density of poly(acrylic acid)/montmorillonite superabsorbent composite on water absorbency". Polymer International 2001, 50, 1050-1053.
Zhang et al. "Synthesis and Properties of Sepiolite/poly(acrylic acid-co-acrylamide) Nanocomposites". Polymer Bulletin 2005, 55, 419-428.
Zhang et al. "On the mechanisms of deactivation of *Bacillus atrophaeus* spores using supercritical carbon dioxide". Journal of Supercritical Fluids 2006 38, 268-273.
Andrews et al. "Effects of sterilisation method on surface topography and in-vitro cell behaviour of electrostatically spun scaffolds." Biomaterials 2007, 28, 1014-1026.
Athanasiou et al. "Sterilization, toxicity, biocompatibility and clinical applications of polyactic acid/ polyglycolic acid copolymers." Biomaterials 1996, 17, 93-102.
Carrascosa et al. "Effect of gamma-sterilization process on PLGA microspheres loaded with insulin-like growth factor-I (IGF-I)." Journal of Biomaterials Applications 2003, 18, 95-108.
Desai et al. "Study of Gamma-Irradiation Effects on Chitosan Microparticles." Drug Delivery 2006, 13, 39-50.
Draganic et al. "Formation of primary yields of hydroxyl radical and hydrated electron in the gamma-radiolysis of water." J. Phys. Chem. 1973, 77, 765-772.
Fischbach et al. "Does UV irradiation affect polymer properties relevant to tissue engineering?" Surface Science 2001, 491, 333-345.
Gogolewski et al. "Sterility, mechanical properties, and molecular stability of polylactide internal-fixation devices treated with low-temperature plasmas." Journal of Biomedical Materials Research 1996, 32, 227-235.
Grimes et al. "The effect of choice of sterilisation method on the biocompatibility and biodegradability of SIS (small intestinal submucosa)." Bio-Medical Materials & Engineering 2005, 15, 65-71.

(56) References Cited

OTHER PUBLICATIONS

Hemmer et al. "Sterilization of Bacterial Spores by Using Supercritical Carbon Dioxide and Hydrogen Peroxide." Journal of Biomedical Material Research (Part B) 2007, 80, 511-518.
Holy et al. "Optimizing the sterilization of PLGA scaffolds for use in tissue engineering." Biomaterials 2001, 22, 25-31.
Huebsch et al. "Analysis of sterilization protocols for peptide-modified hydrogels." Journal of Biomedical Materials Research (Part B) 2005, 74, 440-447.
Kato et al. "Oxidative degradation of collagen and its model peptide by ultraviolet irradiation." J. Agric. Food Chem. 1992, 40, 373-379.
Kelly-Wintenberg et al. "Use of a one atmosphere uniform glow discharge plasma to kill a broad spectrum of microorganisms." Journal of Vacuum Science & Technology a-Vacuum Surfaces and Films 1999, 17, 1539-1544.
Lerouge et al. "Plasma Sterilization: A Review of Parameters, Mechanisms, and Limitations." Plasmas and Polymers 2001, 6, 175-188.
Majewski et al. "Effects of ultraviolet radiation on the type-I collagen protein triple helical structure: A method for measuring structural changes through optical activity." Physical Review E 2002, 65, 031920.
Markowicz et al. "The impact of vacuum freeze-drying on collagen sponges after gas plasma sterilization." Journal of Biomaterials Science 2006, 17, 61-75.
Moioli et al. "Sustained Release of TGFβ3 from PLGA Microspheres and Its Effect on Early Osteogenic Differentiation of Human Mesenchymal Stem Cells." Tissue Engineering 2006, 12, 537-546.
Nair. "Currently practised sterilization methods—some inadvertent consequences." Journal of Biomaterials Applications 1995 10, 121-135.
Noah et al. "Impact of sterilization on the porous design and cell behavior in collagen sponges prepared for tissue engineering." Biomaterials 2002, 23, 2855-2861.
O'Leary et al. "The toxicogenic potential of medical plastics sterilized with ethylene oxide vapors." Journal of Biomedical Materials Research 1968, 2, 297-311.
Ozalp et al. "Controlled release of vancomycin from biodegradable microcapsules." Journal of Microencapsulation 2001, 18, 89-110.
Rutala et al. "Comparative evaluation of the sporicidal activity of new low-temperature sterilization technologies: ethylene oxide, 2 plasma sterilization systems, and liquid peracetic acid." American Journal of Infection Control 1998, 26, 393-398.
Shearer et al. "Effects of Common Sterilization Methods on the Structure and Properties of Poly (D,L Lactic-Co-Glycolic Acid) Scaffolds." Tissue Engineering 2006, 12, 2717-2727.
Zhang et al. "Supercritical carbon dioxide and hydrogen peroxide cause mild changes in spore structures associated with high killing rate." Journal of Microbiological Methods 2007, 70, 442-451.
Casas et al. "Effect of addition of cosolvent on the supercritical fluid extraction of bioactive compounds from *Helianthus annuus* L." Journal of Supercritical Fluids 2007, 41, 43-49.
Charlton et al. "A comparison of the efficacy of lumen-cleaning devices for flexible gastrointestinal endoscopes." Australian Infection Control 2007, 12, 81-90.
Cholvin et al. "General compatibility". Handbook of biomaterials evaluation: Scientific, technical, and clinical testing of implant materials, 2nd edition, 1998, 507-522.
Ding et al. "A new era in pyrogen testing." Trends in Biotechnology 2001, 19, 277-281.
Donlan. "Biofilms and device-associated infections." Emerging Infectious Diseases 2001, 7, 277-281.
Fitzgerald. "Infections of hip prostheses and artificial joints." Infectious Disease Clinics of North America 1989, 3, 329-338.
Gagnon et al. "Endotoxin affinity for provisional restorative resins." Journal of Prosthodontics 1994, 3, 228-236.
Gorbet et al. "Endotoxin: The uninvited guest." Biomaterials 2005, 26, 6811-6817.
Granados et al. "Assessment of parameters associated to the risk of PVC catheter reuse." J Biomed Mater Res 2001, 58, 505-510.
Hagman. "Sterilization." Remington: The science and practice of pharmacy 2005, 776-801.
Heinrich et al. "Endotoxin in fine($PM_{2.5}$) and coarse ($PM_{2.5-10}$) particle mass of ambient aerosols: A temporal-spatial analysis." Atmospheric Environment 2003, 37, 3659-3667.
Joslyn. "Sterilization by heat". Disinfection, sterilization, and preservation, $3^{rd}$ edition, 1983, 27-30, 766-767.
King et al. "The mutual solubilities of water with supercritical and liquid carbon dioxide." Journal of Supercritical Fluids 1992, 5, 296-302.
Knoernschild et al. "Endotoxin adherence to and elution from two casting alloys." The International Journal of Prosthodontics 1994, 7, 22-29.
Kundsin et al. "Detection of Endotoxin on Sterile Catheters Used for Cardiac Catheterization." Journal of Clinical Microbiology 1980, 11, 209-212.
Liu et al. Formation of Water-in-$CO_2$ Microemulsions with Non-fluorous Surfactant Ls-54 and Solubilization of Biomacromolecules. Chem Eur J 2002, 8, 1356-1360.
Martich et al. "Response of man to endotoxin." Immunobiology 1993, 187, 403-416.
Morrison et al. "Current status of bacterial endotoxins." ASM News 1994, 60, 479-484.
Nakagawa et al. "Endotoxin contamination in wound dressings made of natural biomaterials." J Biomed Mater Res 2003, 66, 347-355.
Nelson et al. "Lipopolysacharide affinity for titanium implant biomaterials." The Journal of Prosthetic Dentistry 1997, 77, 76-82.
Novitsky et al. "Factors affecting recovery of endotoxin adsorbed to container surfaces." Journal of Parenteral Science and Technology 1986, 40, 284-286.
Ohno et al. "Lipopolysaccharide interaction with lysozyme: Binding of lipopolysaccharide to lysozyme and inhibition of lysozyme enzymatic activity." The Journal of Biological Chemistry 1989, 264, 4434-4441.
Pabst et al. "Bacterial LPS: A mediator of inflammation." Handbook of Inflammation 1989, 361-393.
Park et al. "Predictors of airborne endotoxin in the home." Environmental Health Perspectives 2001, 109, 859-864.
Raetz. "Biochemistry of endotoxins." Annual Review of Biochemistry 1990, 59, 129-170.
Ragab et al. "Measurement and removal of adherent endotoxin from titanium particles and implant surfaces." J Orthop Res 1999, 17, 803-809.
Ramakrishna. "Safety of technology: Infection control standards in endoscopy." Journal of Gastroenterology and Hepatology 2002, 17, 361-368.
Reyes et al. "Pyrogenic reactions after inadvertent infusion of endotoxin during cardiac catheterizations." Annals of Internal Medicine 1980, 93, 32-55.
Rietschef et al. "Bacterial endotoxins." Scientific American 1992, 267, 54-61.
Rietschel et al. "Bacterial endotoxin: molecular relationship of structure to function." The FASEB Journal 1994, 8, 217-225.
Rioufol et al. "Quantitative determination of endotoxins released by bacterial biofilms." Journal of Hospital Infection 1999, 43, 203-209.
Robinson et al. "*Porphyromonas gingivalis* endotoxin affinity for dental ceramics." Journal of Prosthetic Dentistry 1996, 75, 217-227.
Rudnick et al. "An outbreak of pyrogenic reactions in chronic hemodialysis patients associated with hemodialyzer reuse." Artif Organs 1995, 19, 289-294.
Rutala et al. Reprocessing endoscopes: United Stated perspective. Journal of Hospital Infection 2004, 56, 27-39.
Sweadner et al. "Filtration removal of endotoxin (pyrogens) in solution in different state of aggregation." Applied and Environment Microbiology 1977, 34,382-385.
Tessarolo et al. "Efficiency in endotoxin removal by a reprocessing protocol for electrophysiology catheters based on hydrogen peroxide plasma sterilization." International Journal of Hygiene and Environmental Health 2006, 209, 557-565.
Tsuji et al. "Dry heat destruction of LPS: Drug heat destruction kinetics." Applied and Environment Microbiology 1978, 36, 710-714.

(56) References Cited

OTHER PUBLICATIONS

Weary et al. "A manufacturer's guide to depyrogenation." BioPharm Manuf 1988, 1, 22-29.

M. Belton, "Allergen impermeable covers appear clinically ineffective in the management of adult asthma patients." N Engl J. Med. 2003, 349, 3.

Bischoff et al., "Assessment of mite numbers: new methods and results." Experimental & Applied Acarology 1992, 16, 1-14.

de Boer et al., "The decay of house dust mite allergens, Der p I and Der p II, under natural conditions." Clin Exp Allergy 1995, 25, 765-770.

Eastoe et al., "Self-assembly in green solvents". Physical Chemistry Chemical Physics 2005, 7, 1352-1362.

Ginty et al., "Mammalian cell survival and processing in supercritical $CO_2$". Proceedings of the National Academy of Sciences 2006, 103, 7426-7431.

John et al., "Functional effects of the inhibition of the cysteine protease activity of the major house dust mite allergen der p 1 by a novel peptide-based inhibitor". Clinical and Experimental Allergy 200, 30, 784-793.

Jovanovic et al., "Stabilization of proteins in dry powder formulations using supercritical fluid technology". Pharmaceutical Research 2004, 21, 1955-69.

Kauffman et al., "House dust mite major allergens Der p 1 and Der p 5 activate human airway-derived epithelial cells by protease-dependent and protease-independent mechanisms." Clinical and Molecular Allergy 2006, 4:5.

Kawamoto et al., "Toward elucidating the full spectrum of mite allergens—state of the art." Journal of Bioscience and Bioengineering 2002, 94, 285-298.

Kort et al., "Four-year stability of Der p 1 in house dust under simulated domestic conditions in vitro." Allergy 1994, 49, 131-133.

Lau et al., "Placebo-controlled study of the mite allergen-reducing effect of tannic acid plus benzyl benzoate on carpets in homes of children with house dust mite sensitization and asthma." Pediatric Allergy and Immunology 2002, 13, 31-36.

Sidenius et al., "Decay of house-dust mite allergen Der f 1 at indoor climatic conditions." Annals of Allergy, Asthma & Immunology 2002, 89, 34-37.

Woodcock et al., "Control of Exposure to Mite Allergen and Allergen-Impermeable Bed Covers for Adults with Asthma." N Engl J Med 2003, 349, 225-236.

Zagrobelny et al., "In situ studies of protein conformation in supercritical fluids: Trypsin in carbon dioxide". Biotechnology Progress 1992, 8, 421-423.

Zhang et al., "Sterilizing *Bacillus pumilus* spores using supercritical carbon dioxide". Journal of Microbiological Methods 2006, 66, 479-485.
Zhang et al., "Sterilization using high-pressure carbon dioxide". Journal of Supercritical Fluids 2006, 38, 354-372.

* cited by examiner

METHODS AND COMPOSITIONS FOR ELIMINATING ALLERGENS AND ALLERGEN-PRODUCING ORGANISMS

PRIORITY INFORMATION

The present application claims priority to U.S. Provisional Patent No. 61/340,897 filed on Mar. 24, 2010 titled "Methods and Compositions for Eliminating Allergens and Allergen-Producing Organisms" of Matthews, et al. and U.S. Provisional Patent No. 61/398,812 filed on Jul. 1, 2010 titled "Reducing Dust Mite Populations and Allergen Levels Using High Speed Dry Ice Jets" of Matthews, et al., the disclosures of which are incorporated by reference herein.

FIELD OF INVENTION

The technology relates to the prevention and removal of harmful allergens from substrates in a home leading to improved air quality to inhibit allergic reactions and other health problems in humans.

BACKGROUND OF INVENTION

More than 50 million Americans suffer from allergies, making them the sixth leading cause of chronic disease in the United States, and responsible for 3.8 million lost work or school days per year. Common house dust is a leading cause of allergies. Although there are many components in house dust that may be allergenic, the most common culprit by far is the dust mite, which is second only to pollen overall in causing allergic reactions. More than 15 groups of house dust mite allergens (proteins) have been identified from extracts and feces of dust mites. The group 1 and group 2 proteins are the major allergens, accounting for 60 to 90% of the activity.

Furthermore, dust mite allergens are closely related to the onset of asthma. Asthma is a serious and potentially fatal condition that is especially critical in children under age 13. The American Lung Association estimates that 32.5 million Americans (approx. 11.2%) have been diagnosed with asthma. 14.2% of American children between 5 and 17 years of age had asthma is in 2005. It has been shown that most children with exacerbation of asthma have been exposed to high levels of mite allergens, and that continuous exposure can result in hospital readmission. The highest levels of allergens are found in bedding (blankets, sheets, spreads, pillow cases, etc.), placing humans at high risk of inhaling the offending proteins. A nationwide survey conducted by the National Institute of Environmental Health Sciences (NTRHS) and the US Department of Housing and Urban Development in 1998 and 1999 reports that 84% of U.S. homes have detectable levels of mite allergens; about half have levels sufficient to trigger allergic reactions; and a quarter of U.S. homes have high enough allergen level to cause asthma. The cost of asthma in 2007 is projected to reach $19.7 billion ($14.7 direct, $5 indirect). In New York's Harlem neighborhood, 25.5% of children under age 13 suffer from asthma. The sensitization level of the group 1 allergen in adults is 2 µg allergen/g dust, and 10 µg allergen/g dust enhances asthma symptoms. For children, the sensitization level could be as low as 50 ng/g, far below the general sensitization level.

Dust mites are eight-legged arachnids, relatives of the spider. The American house dust mite (*Dermatophagoides farinae*, Df) and the European house dust mite (*Dermatophagoides pteronyssinus*, Dp) are the two most common species in the United States. Dust mites progress through the egg, larval and nymph stages in about 25 days to become microscopic adults about 0.3 mm in length. Adults live two to three months, during which time the female can lay 25 to 50 eggs every two to three weeks. They feed on shed scales of human skin. Only environments with a relative humidity of less than 50% year round are safe from these allergy causers. Mites live in carpet, upholstered furniture, and bedding. The allergenic proteins are actually present in dust mite feces and each dust mite produces about twenty waste particles per day. More than 100,000 particles can be present in a single gram of dust. Particles continue to cause allergy symptoms long after the dust mites themselves are dead. Mite allergens can cause or exacerbate three major diseases: asthma, perennial rhinitis, and atopic dermatitis. The consequences of which can be fatal.

More than 15 groups of house dust mite allergens have been identified from extracts and feces of Dp and Df dust mites. The group 1 (Der p 1 and Der f 1) and group 2 (Der p 2 and Der f 2) proteins are the major allergens, accounting for 60 to 90% of IgE binding activity of the dust mite sera. The group 2 allergen levels are comparable to the levels of the group I allergens. The group 1 allergens are proteins (MW 25 kDa) with cysteine protease activity. Proteolytic activity is an important factor for sensitization by Der p 1. Der p 1 cleaves the CD23 IgE receptors on B-cells and the CD25 subunit of the IL-2 receptor on T-cells, which further promote the Th2 response and IgE-mediated hypersensitivity (allergy).

At present, there are few effective options for patients with severe allergic or asthmatic reactions. Allergen avoidance (i.e. relocation to allergy-free environments) has been shown to result in reduced asthma symptoms. Obviously, moving people and families into special environments is both expensive and socially disruptive. Conventional allergen avoidance measures include washing of fabrics in hot water, using allergen impermeable covers, regular vacuuming, and elimination of carpet and upholstered furnishings. Washing is recommended to control dust mite allergen levels. Washing can remove soluble allergens, and hot water will kill dust mites if the temperature is higher than 55° C. Many items of bedding cannot be washed in a household washer, and ordinary U.S. household washers operate with warm or cold water that does not ensure mite death. *D. pteronyssinus* is highly resistant to warm water, detergent and chlorine. A 4 hour soak in a 35° C. detergent and chlorine (0.35%) solution achieved only 34% mortality of *D. pteronyssinus*. Even with the addition of 0.03% benzyl benzoate, approximately 50 out of 10,000 mites survived. Additional concerns about washing include the transference of mites between infested and mite-free items, and the fact that some fabrics will shrink or be damaged when washed at 55° C. Chemical-based dry cleaning effectively kills mites and can be used to clean delicate clothing and some bedding items, but has been shown to reduce the allergen activity by only 70%, because the residual proteins are not deactivated by dry cleaning. Semi-impermeable mattress covers are said to control allergen levels for at least 12 weeks, leading to improved symptoms. However, this method is not low-maintenance as it requires regular washing of the case at T>55° C. and periodic wiping.

Using acaricides to kill dust mites, therefore eliminating the source of allergens, is another method that has been proposed to reduce allergen levels. Heller-Hauput and Busvine tested 15 chemicals for ability to kill *D. farinae*. In the order of potency, Lindane, pirimiphosmethyl, and benzyl benzoate are the most effective. Toxicity studies and a history of use for treatment of scabies indicate that Lindane and benzyl benzoate can safely be used to kill dust mites. However, acaricides do not deactivate residual allergy-causing mite proteins.

Solid benzyl benzoate foam and powders (60 g/m2, then vacuumed) have been tested on mattresses and blankets in Germany for their efficiency of reducing Der p 1 and der f 1 allergens. The tests revealed that powered benzyl benzoate only works on blankets possibly due to the difficulty of the solid material penetrating the mattresses which are much thicker than blankets. A similar study in Italy reported that benzyl benzoate in foam form is also not effective in decreasing dust mite allergen again possibly due to insufficient penetration.

Prior art indicates that dense phase $CO_2$ can kill various types of cells, including microorganisms (bacteria, bacterial spores, fungus) and mammalian cells, with the help from selected liquid chemicals including water and hydrogen peroxide. It takes hours to kill resistant species such as bacterial spores. However, it only takes minutes to kill animal cells such as mammalian cells. Therefore, dense phase $CO_2$ can kill living dust mites quickly.

It is the protein secreted by dust mites that are the main cause of allergic reactions and asthma. These proteins secreted by *Dermatophagoides pteronyssinus* include a spectrum of mite allergens denominated as der p1 to der p9. Among these, der p1 and der p2 are the major allergens. Partial inactivation of proteins by dense phase $CO_2$ has been widely documented in the literature. However, no complete inactivation of enzymes with $CO_2$ has been previously reported.

Current state of the art measures to prevent mite allergen-induced diseases include frequent vacuuming with high filtration vacuum cleaners, UV light irradiation, topical application of an insecticide to kill the dust mite, covering all beds with micro-porous dust-proof or allergen impermeable covers, weekly washing of bedding with hot water and freezing non-washable beddings overnight, and removing carpets from all rooms. However most prior art suffers from many drawbacks. Vacuum cleaners and insecticides suffer from the inability to penetrate deep into carpets. Also, carpets usually cannot be removed and frozen; or be washed with hot water. It is not feasible to cover entire household carpets with impermeable covers. In addition, water washing, even with hot water, will not kill dust mites; and impermeable covers appear clinically ineffective in adults with asthma.

As such, a need exists for the eradication of dust mites that overcomes the disadvantages of prior art methods.

SUMMARY

Objects and advantages of the invention will be set forth in part in the following description, or may be obvious from the description, or may be learned through practice of the invention.

Methods are generally provided for making a treatment composition by loading active components into a high pressure vessel and pressurizing the high pressure vessel with carbon dioxide to reach a pressure within the high pressure vessel of about 400 pounds per square inch to about 1,070 pounds per square inch. The active components can include a protein denaturant and a surfactant, and optionally an acaricide. In one particular embodiment, this method can be used to clean a substrate, by loading the substrate into the high pressure vessel prior to pressurizing with carbon dioxide.

Treatment compositions are also generally provided that include (e.g., comprise, consist essentially of, or consist of) a surfactant, a protein denaturant, an optional acaricide, and a dense phase carbon dioxide, wherein the composition has a pressure of about 400 pounds per square inch to about 1,070 pounds per square inch.

Methods are also generally provided for treating a substrate to clean it from dust mites by delivering dry ice particles (e.g., including frozen carbon dioxide and optionally an acaricide, a protein denaturant, and/or a surfactant) to the substrate, and vacuuming the substrate.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1:
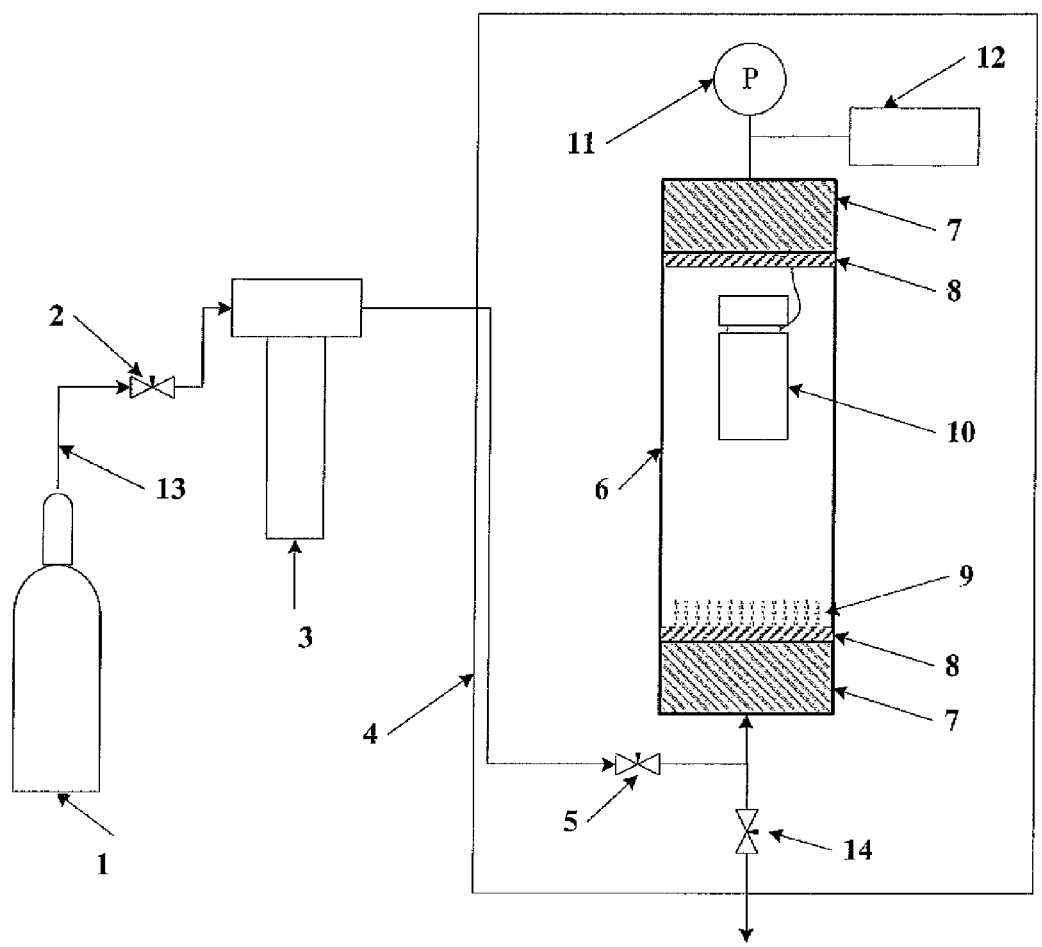
FIG. 1 shows an exemplary allergen denaturation apparatus.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

In general, treatment compositions, along with the methods of making and using, are generally disclosed for eradicating living dust mites and denaturing allergenic proteins secreted by dust mites in substrates that are known to harbor these allergenic sources. For example, in one embodiment, the composition includes a combination of pressurized carbon dioxide, a surfactant, and/or a protein denaturant. In particular embodiments, the compositions include pressurized carbon dioxide, surfactants, acarcides, and/or protein denaturants, such that the compositions are configured to kill dust mites and/or denature allergenic proteins and/or solubilize or remove allergenic proteins and endotoxins. Additionally, methods and compositions are generally disclosed for solubilization and removal of dust mite allergens and bacterial endotoxin with compositions comprising the combination of pressurized carbon dioxide and a surfactant.

The methods and treatment compositions presently disclosed generally use dense phase carbon dioxide ($CO_2$) as a solvent medium. This dense phase $CO_2$ uniquely aids in the formation and delivery of microemulsions of surfactants and/or oxidizing molecules (e.g., hydrogen peroxide, chlorine dioxide, or mixtures thereof). The oxidizing molecules can subsequently denature allergenic proteins and enhance the killing of allergen producing organisms. In one particular embodiment, the use of dense phase $CO_2$, with surfactants and mite allergen denaturant (e.g., tannic acid), promotes the inactivation of allergenic proteins.

I. Composition

As stated, treatment compositions are disclosed that generally include pressurized carbon dioxide, a surfactant, an acaricide, and/or a protein denaturant. Other allergy controlling agents (e.g., amines, hops extracts, anti-allergenic iodo derivatives, quaternary ammonium compounds, glycol ether, glycol ether ester, or mixtures thereof) can also be included in the composition to promote the inactivation of allergenic proteins.

The term "dense phase carbon dioxide" can also be referred to as "high-pressure carbon dioxide," "high-pressure $CO_2$," "dense-phase carbon dioxide," and "dense-phase $CO_2$" refers to pressurized carbon dioxide, either in its liquid state near, but below, the critical temperature and near the critical pressure or to supercritical carbon dioxide, above both the critical temperature and critical pressure. For example, in one aspect, the pressure can be from about 400 pounds per square inch (about 27.6 bar) to about 4,000 pounds per square inch (about 275 bar). In another aspect, the pressure can be from about 500 pounds per square inch (about 34.5 bar) to about 850 pounds per square inch (about 58.6 bar). In a further aspect, the pressure can be from about 600 pounds per square inch (about 41.36 bar) to about 750 pounds per square inch (about 51.7 bar). Alternatively, the pressure can be about 2000 pounds per square inch to about 4000 pounds per square inch. The temperature range can be about 0° C. to about 60° C., such as from about 10° C. to about 25° C.

One or more surfactants can be included with the $CO_2$ solvent to enhance the formation of micro emulsions. The surfactant(s) that can be included within the compositions include, but are not limited to, fluorosurfactants, ionic surfactants, silicon-based surfactants (e.g., siloxane surfactants), hydrocarbon surfactants, or mixtures thereof. In particular embodiments, the surfactant(s) can have a concentration range of about 0.2% by volume to about 10% by volume of the treatment composition, such as about 0.5% by volume to about 5% by volume.

Acaricides are pesticides that kill members of the Acari group, which includes ticks and mites. Their inclusion in the composition enhances the elimination of allergy producing organisms (e.g., mites). Suitable acaricides can include, but are not limited to permethrin, benzyl benzoate, ivermectin, antibiotic miticides, carbamate miticides, formamidine miticides, organochlorine, organophosphate miticides, diatomaceous earth, dicofol, or mixtures thereof. Particularly suitable acaricides that can be included within the composition include, but are not limited to, benzyl benzoate, permethrin, or mixtures thereof. In particular embodiments, the acaricide(s) can have a concentration range of about 0.01% by volume to about 5% by volume of the treatment composition, such as about 0.05% by volume to about 3% by volume.

The protein denaturant of the compositions can be included as a mite allergen denaturant, targeting the proteins and other organic compounds formed by mites. Such protein denaturants can include, but are not limited to, ethanol, hydrogen peroxide, benzyl benzoate, and tannic acid. In addition, synthetic non-oxidizing protein inhibiters, such as PTL 11028, a peptide-based inhibitor, can be included in the composition to promote the inactivation of allergenic proteins. In particular embodiments, the protein denaturant(s) can have a concentration range of about 0.001% by volume to about 3% by volume of the treatment composition, such as about 0.01% by volume to about 1% by volume.

II. Methods of Making the Treatment Compositions

According to one particular embodiment, the treatment compositions can be made by loading the desired active components (e.g., protein denaturant(s), surfactant(s), acaricide(s), etc., and mixtures thereof) into a high pressure vessel and pressurizing the vessel with $CO_2$ gas. For example, the internal pressure within the vessel, upon adding $CO_2$ gas can be about 400 pounds per square inch (about 27.6 bar) to about 1,070 pounds per square inch (about 73.7 bar), as discussed above.

In one particular embodiment, the $CO_2$ gas, when loaded into the vessel, has a purity of about 90% by volume or more (e.g., about 95% to 100% by volume). For instance, the $CO_2$ gas can be substantially pure $CO_2$ gas, as in substantially free from other molecules. As used herein, the term "substantially free" means no more than an insignificant trace amount present and encompasses completely free (e.g., 0% up to 0.01% by volume).

The high pressure vessel is generally designed to withstand the relatively high pressures involved with the dense phase carbon dioxide composition, such as up to about 1500 pounds per square inch. In one particular embodiment, the vessel is large enough to accommodate the substrates themselves. For example, the vessel can be a modified washer machine-like vessel configured to withstand relatively high pressures.

An exemplary allergen denaturation apparatus is depicted in FIG. 1 as used in the Examples. Gas for preparation of a high-pressure or supercritical fluid is supplied to the high pressure vessel 6 from gas tank 1 via gas line 13. Supercritical $CO_2$ refers to pressurized, fluid carbon dioxide at or above the critical temperature (about 31.1° C.) and at or above the critical pressure (about 73.8 bar), while supercritical fluid refers to a pressurized, fluid gas at or above the critical temperature and at or above the critical pressure. High-pressure fluid and dense-phase fluid refer to pressurized, liquid gas near but below the critical temperature and near but below the critical pressure. In one aspect, the pressure can range from 35% to 99% of the critical pressure of the gas (e.g. from 40% to 85% of the critical pressure, from 60% to 75% of the critical pressure.) Gas line 13 is an air-tight hollow tube constructed so as to withstand the required pressures for high-pressure and supercritical fluids. Pump inlet valve 2 is positioned in fluid communication with gas line 13 and positioned intermediate gas tank 1 and syringe pump 3. Accordingly, pump inlet valve 2 can control the flow of gas from gas tank 1.

Syringe pump 3 functions to provide gas from gas tank 1 to high pressure vessel 6 as well as to provide the pressures for high-pressure or supercritical fluids. In one aspect, syringe pump 3 is calibrated to provide a selected pressure. Inlet valve 5 can control the flow of gas from syringe pump 3 and is located along gas line 13 between syringe pump 3 and high pressure vessel 6.

The high pressure vessel 6 is placed inside an environmental chamber 4. Environmental chamber 4 is programmed to raise or lower the temperature with desired fashion or to keep constant temperature. High pressure vessel 6 has one hand-tight cap 7 and one stainless steel filter 8 at each end of the vessel body. Liquid additives 9 are directly placed on the lower filter 8. When $CO_2$ is supplied through the gas line 13 and passes through the lower filter 8, $CO_2$ bubbles through the liquid additives 9 and solubilize the additives into $CO_2$ phase. The pressure inside the high pressure vessel is measured with a pressure gauge 11 connected to the top cap 7. A rupture disc 12 is also connected to the top cap 7 to prevent over pressurizing the vessel 6. Vent valve 14 is connected to the bottom cap 7 of the vessel and is used to release $CO_2$ pressure and vent liquid additives 9 from the vessel 6 at the end of an experiment.

Proteins or allergens are contained in a glass vial 10. The glass vial 10 is attached to the top filter with a string and suspended in the $CO_2$ phase. $CO_2$ can freely enter and leave the vial through the opening on top of the vial.

III. Methods of "Washing" Substrates in the Treatment Composition

Methods are also generally disclosed for using the disclosed compositions for denaturing, solubilizing, and removing allergenic proteins. Specifically, the compositions can be used to help eradicate substrates from mites and their by-products. The substrates applicable to this method include, but are not limited to, beddings (e.g., pillows, comforters, mattresses, pads, covers), carpets, soft furnishings (e.g., area rugs, curtains, drapes), and/or furniture cushions (e.g., pillows, throws, seat covers, furniture covers).

In one particular embodiment, the substrate(s) can be loaded into a high pressure vessel, which is then filled with the treatment composition. For example, the protein denaturant and/or surfactant and/or acaricides and/or other components can be loaded into the high pressure vessel after or with the substrate(s), and $CO_2$ gas can be used to pressurize the gas. The vessel can be held at the desired conditions (temperature, pressure, agitation) as discussed above, prior to finally releasing the pressure. For instance, in a particularly suitable "washing cycle", the substrate can be exposed to the treatment composition for a period about an hour or less, such as about 20 minutes to about 45 minutes, with the treatment pressure being about 500 pounds per square inch to about 1000 pounds per square inch at a temperature of about 5° C. to about 30° C. Finally, the substrate(s) can be rinsed with high pressure $CO_2$ gas to remove residual components (e.g., protein denaturant and/or surfactant and/or acaricides, etc.).

IV. Methods Using Dry Ice Pellets

Alternatively, dry ice pellets (i.e., frozen carbon dioxide) can be used to loosen and/or kill dust mites and their feces in a substrate (e.g., a carpet). For example, solid dry ice particles (e.g., created according to the method described in U.S. Pat. No. 7,293,570 of Jackson, which is incorporated by reference herein) can be ejected from nozzles. For example, the nozzles can generate sheer stress up to 55 MPa. These solid dry ice particles impact with dust mites and dust mite feces attached to carpet fibers and dislodge them from the carpets. Next, a high efficient vacuum system can remove the dislodged dust mites and mite feces which contain dust mite allergens. In addition, by impacting dust mites with ultra low temperature dry ice particles (e.g., −109° F.), the dust mites will be instantaneously frozen and killed. At room temperature, dry ice particles sublime quickly to gaseous carbon dioxide, leaving no solvent residuals.

The dry ice particles can, in one embodiment, have a size (i.e., an average diameter) of 1 micron to about 500 microns, such as about 10 microns to about 200 microns.

In one particular embodiment, an acaricide, surfactant, and/or protein denaturant (such as described above) can be pre-dissolved in liquid $CO_2$ upstream of the nozzle. For example, upon formation of dry ice particles including an acaricide, the acaricide is frozen into the particles and is forced deep into the carpet by the velocity of the stream. The $CO_2$ then sublimes, leaving the less-volatile acaricide safely and deeply imbedded into the carpet. The acaricide serves to prevent re-infestation of dust mites, thus providing even longer-term protection.

As such, this method allows deeper and more thorough cleaning of carpets than conventional vacuuming or UV irradiation. In addition, the method presented in this invention will greatly reduce the dust mite population and allergen levels in carpets. Treatment of such articles with the process disclosed herein will reduce the cost of treatment and alleviate suffering in adults, children, and infants who are susceptible to allergies.

Thus, a method of treatment can include using solid carbon dioxide particles to loosen dust mites from carpets so that the dust mites can be removed with vacuum and/or using solid carbon dioxide particles to kill dust mites by lowering their temperature to about −78.5° C. or lower. Additionally, the methods can include using solid carbon dioxide particles to deliver an acaricide into the carpet, allowing residual acaricide to inhibit re-infestation of dust mites.

The components used to prepare the disclosed compositions as well as the compositions themselves used within the methods are disclosed herein. It is understood that when combinations, subsets, interactions, groups, etc. of these materials are disclosed, the various individual and collective combinations and pe mutation of these compounds may are specifically contemplated even if they are not explicitly described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures can ultimately achieve the same result.

EXAMPLES

The following examples are meant to illustrate the invention described herein and are not intended to limit the scope of this invention. Current laboratory work on inactivating enzymes has shown that 80-90% of enzymatic activity of trypsin, a model protease, can be reduced with supercritical $CO_2$ containing a microemulsion of selected oxidizing ($H_2O_2$) and non-oxidizing (1% tannic acid) agents.

Example of Protein Denaturation

Proteins/Allergens

In this example, trypsin was used as a model protein to demonstrate the capability of the disclosed allergen denaturation method. The trypsin was extracted from bovine pancreas and supplied as salt free lyophilized powder.

Quantifying Denaturation

The enzymatic activity of trypsin was quantified with a BAEE (N-a-Benzoyl-L-Arginine Ethyl Ester) assay: The amount of trypsin was measured by the rate of increase in the optical density of BAEE solution as a result of enzymatic degradation of BAEE. Four reagents were prepared for the BAEE assay. Reagent A was 67 mM sodium phosphate buffer at pH 7.6 at 25° C. Reagent B was 25 mM BAEE in Reagent A. Reagent C was 1 mM hydrochloride acid. And Reagent D was freshly made trypsin sample in cold Reagent C.

Three milliliters of Reagent B and 0 2 mL of reagent D were quickly mixed inside a cuvette and measured with a IN-V is spectrophotometer. The increase in the optical density at 253 nm was measured for approximately 5 min and compared with a standard sample to determine the enzymatic activity of the trypsin sample.

Procedure

Prior to the denaturation experiment, milligram levels of trypsin powder were transferred into a clean 2 mL glass vial. The septum of the vial cap had been replaced with a nylon filter to prevent escapes of trypsin particles, and to allow the free flow of $CO_2$ into and out of the vial. Three milliliters of a surfactant LS-54 and 2 mL of selected protein denaturant (e.g. ethanol, 1% tannic acid, 30% hydrogen peroxide) were placed directly on top of the lower filter. The surface tension of this liquid mixture prevented it from flowing downwards through the filter. The trypsin containing vial was attached to the top filter with a cotton string to prevent direct contact between liquid denaturant and protein, so as to avoid false positive results.

At the beginning of the experiment, the environmental chamber was preheated to desired temperature (40° C. and 60° C. in this example, but other temperatures can be used) and the syringe pump raised the $CO_2$ pressure to a pre-set value (e.g. 4000 psi). Then the vent valve was closed and inlet valve was slowly opened to allow $CO_2$ to flow through the filter and the liquid mixture, where the liquid mixture dissolved into the $CO_2$ phase and create water-in-$CO_2$ micro-emulsions.

The temperature and pressure were maintained for the predetermined amount of time. Then the inlet valve was closed. The pressure chamber was slowly depressurized through the vent valve untile the vessel reached atmospheric pressure.

The trypsin containing vial was immediately removed from the vessel. Trypsin was dissolved in cold 1 mM hydrochloric acid solution and assayed with the BAEE procedure.

Results and Discussion

Figure 2:
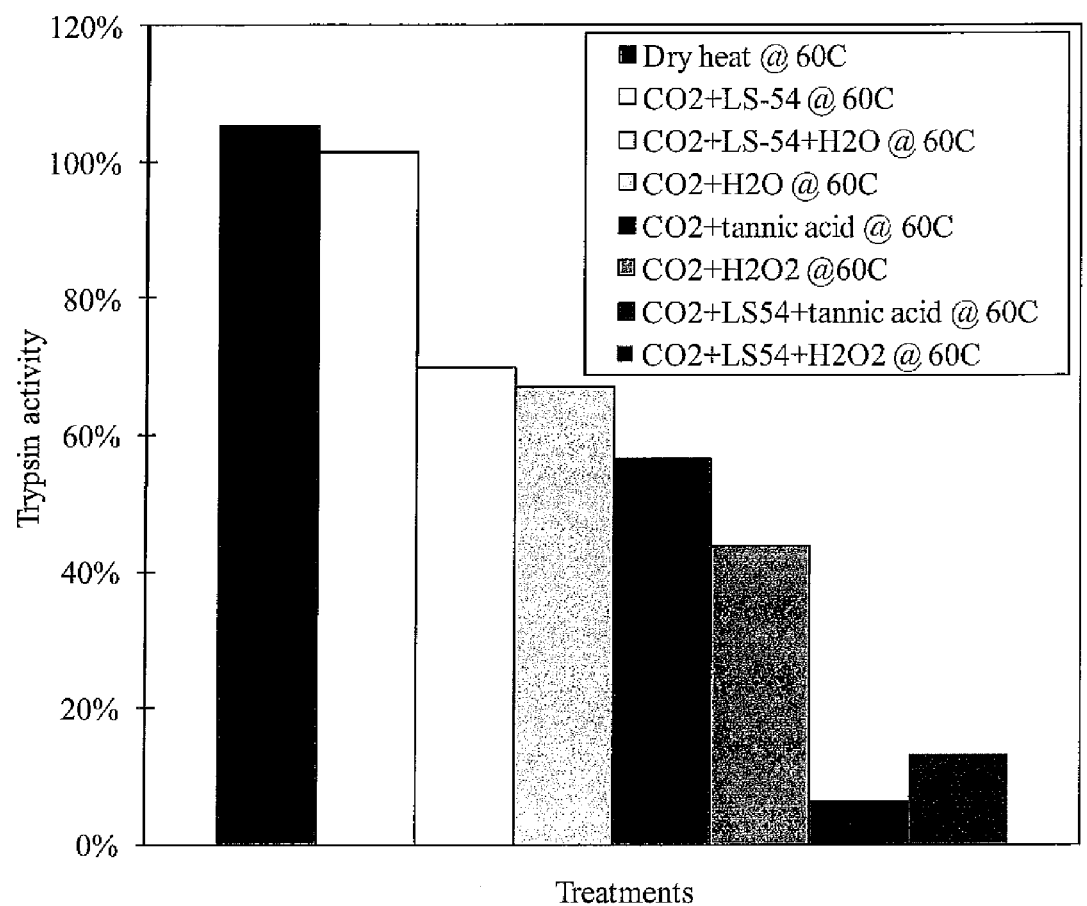
FIG. 2 shows a chart of inactivation results of $scCO_2$ with different additives at 4000 psi, 60° C., 5 hrs according to the Examples of the present disclosure.
Figure 3:
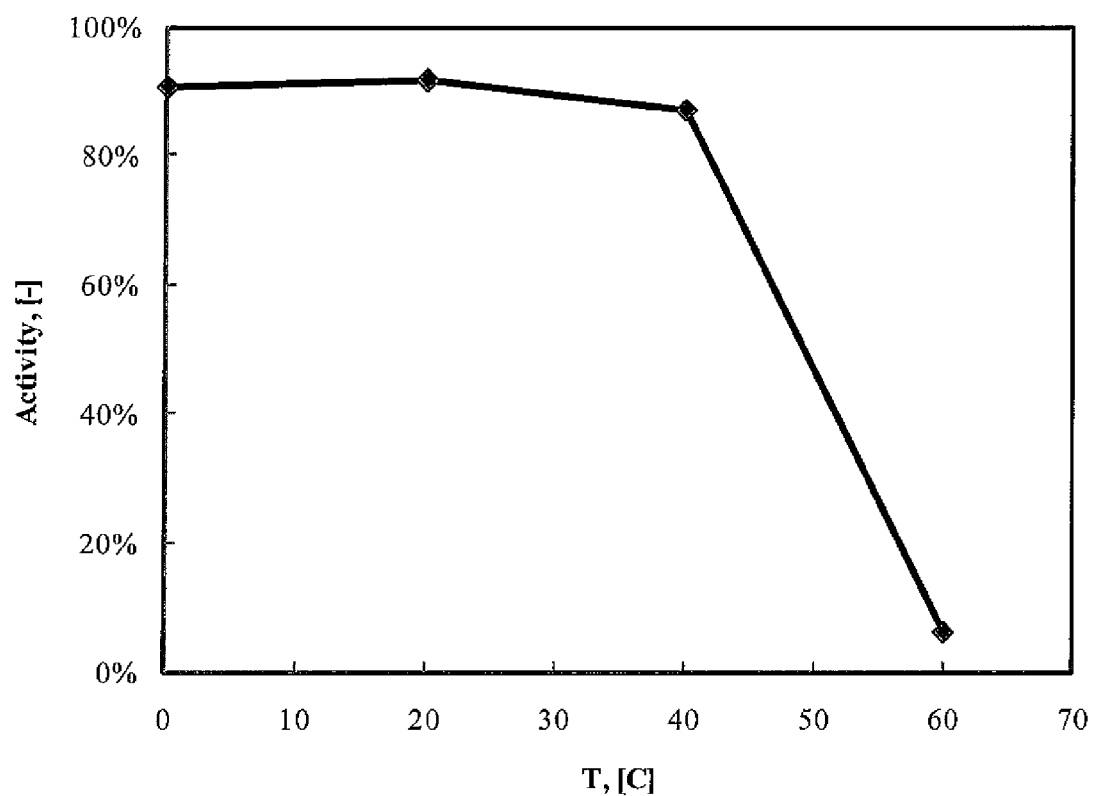
FIG. 3 shows a chart of temperature dependence of $CO_2$+ LS-54+1% tannic acid treatment (4000 psi, 5 hrs) according to the Examples of the present disclosure.

Different additives and combinations among them (water, 30% $H_2O_2$, 1% tannic acid, LS-54, LS-54+$H_2O$, LS-54+1% tannic acid, LS-54+30% $H_2O_2$) were examined for their efficacy of denaturing trypsin at 4000 psi, 60° C. for 5 hours. Among these additives, water is reported to be important in denaturation of proteins in compressed $CO_2$; $H_2O_2$ itself is an oxidant and was used in a supercritical sterilization process; aqueous 1% tannic acid is an effective protein denaturant, widely used in allergy prevention; LS-54 is a carbohydrate surfactant with proven solubility and micelle forming ability in sc$CO_2$. Due to the low solubility of water, $H_2O_2$ and tannic acid in sc$CO_2$, water-in-$CO_2$ micro-emulsion formed by LS-54 is an effective vehicle to deliver protein denaturant in the substrates. The inactivation results of these additives are shown in FIG. 2 (in order from left to right, the bars represent treatment compositions of: (1) Dry heat at 60° C.; (2) $CO_2$ and LS-54 at 60° C.; (3) $CO_2$, LS-54, and water at 60° C.; (4) $CO_2$ and water at 60° C.; (5) $CO_2$ and tannic acid at 60° C.; (6) $CO_2$ and hydrogen peroxide at 60° C.; (7) $CO_2$, LS-54, and tannic acid at 60° C.; and (8) $CO_2$, LS-54, and hydrogen peroxide at 60° C.).

Approximately 90% reduction of the enzymatic activity of trypsin was achieved under two conditions, namely sc$CO_2$+LS54+tannic acid (93.6%) and sc$CO_2$+LS54+$H_2O_2$ (87.0%). Visual inspection of the processed glass vial reveal that the inner surface was completely wetted, indicating successful formation of microemulsion and penetration of microemulsion through the filters in the vial cap. These results proved the importance of the surfactant in this trypsin denaturation process.

Dry heat at 60° C. did not reduce the activity of trypsin, indicating that trypsin is stable at temperatures up to 60° C. Trypsin processed with sc$CO_2$ and of LS-54 has the same activity as untreated trypsin. Deionized water+sc$CO_2$, and the combination of LS-54+deionized water+sc$CO_2$, have similar capacities to reduce trypsin activity to between 60% and 70%, confirming the observation of many other researchers that adding excessive amount of water causes partial denaturation of proteins. This degree of inactivation has significant impact on applications such as enzymatic catalyzed reactions. However, higher or complete inactivation is needed for the purpose of inactivating unwanted proteins (allergens).

One percent tannic acid, a common protein denaturant, in, sc$CO_2$ does not significantly reduce trypsin activity, compared to sc$CO_2$+water and sc$CO_2$+LS-54+water. This is an indication that tannic acid does not have sufficient solubility in sc$CO_2$ to inactivate trypsin, so the majority of the inactivation observed with 1% tannic acid was due to the dissolved water in sc$CO_2$. Adding 30% $H_2O_2$ into sc$CO_2$ further reduced the protein activity to approximately 40%. This demonstrates that at least part of the protein was denatured from the oxidation reaction by the dissolved $H_2O_2$ in sc$CO_2$. Again, due to the low solubility of $H_2O_2$ in sc$CO_2$, the $H_2O_2$ concentration is not sufficiently high enough to completely inactivate trypsin.

Another series of preliminary experiments of $CO_2$+LS54+tannic acid was carried out between 0° C. to 60° C. to explore the effects of process temperature, because lower temperature is preferred to reduce energy consumption and preserve the substrates (Error! Reference source not found.). No significant inactivation of trypsin was observed at temperatures ≤40° C. Considering that trypsin loses most of its activity at 60° C., there seems to be a temperature barrier between 40° C. and 60° C. in the current experimental settings indicating that there is a synergistic effect of $CO_2$ and elevated temperature.

One more preliminary experiment with sc$CO_2$+LS54+tannic acid was conducted with shorter exposure time (4 hours). Trypsin lost only 55% of its activity, compared to the >90% of activity lost after 5 hours which demonstrates that long exposure is required to form LS54 microemulsion in sc$CO_2$. Addition of agitation increases mass transfer from the liquid phase to supercritical $CO_2$, and might accelerate the formation of microemulsion and reduce the time to inactivate trypsin.

In conclusion, the feasibility of reducing >90% activity of a model protein trypsin, with compressed $CO_2$ and selected surfactant and protein inactivation agents. This process is temperature dependent with a synergistic effect of $CO_2$ and elevated temperature. It is further illustrated that without agitation, long exposure is needed to achieve high degree inactivation of proteins.

Figure 4:
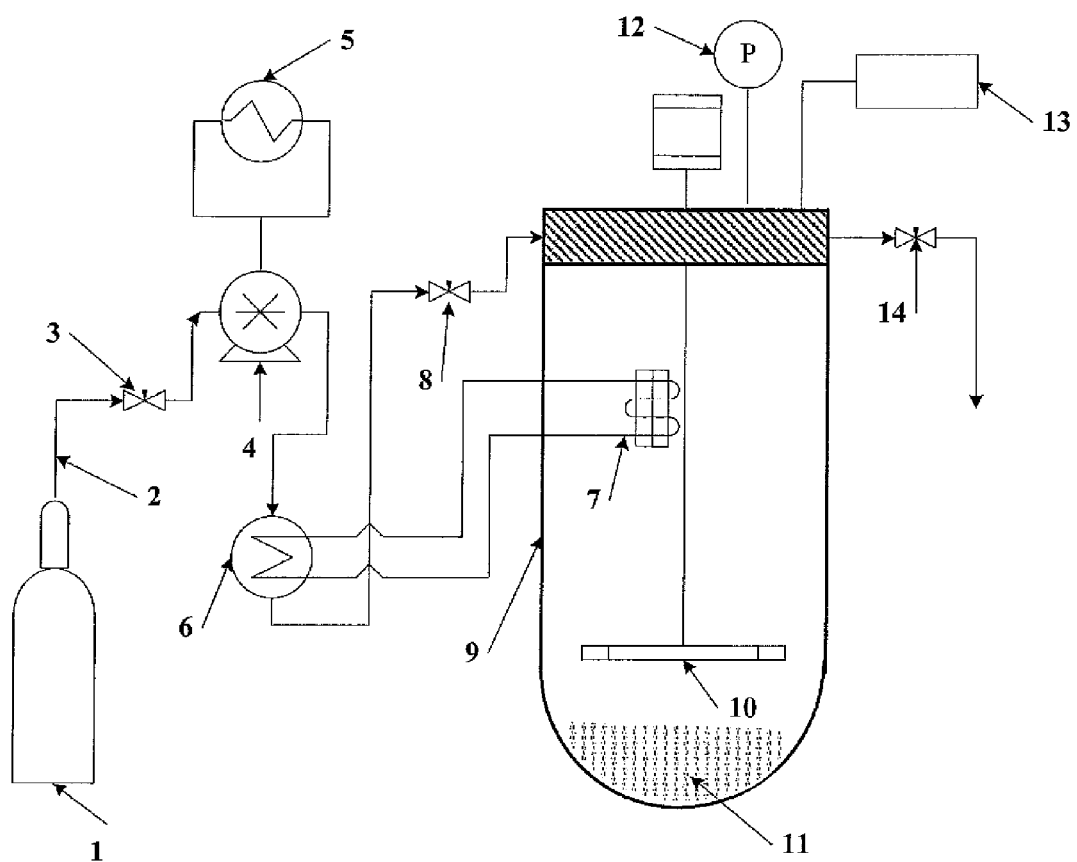
FIG. 4 shows an exemplary allergen and endotoxin solubilization and removal apparatus according to the Examples of the present disclosure.

An exemplary allergen and endotoxin solubilization and removal apparatus is depicted in FIG. 4. Gas for preparation of a high-pressure or supercritical fluid is supplied to the $CO_2$ cleaning vessel 9 from gas tank 1 via gas line 2. Gas line 2 can be an air-tight hollow tube constructed so as to withstand the required pressures for high-pressure and supercritical fluids. Pump inlet valve 3 can be positioned in fluid communication with gas line 2 and positioned intermediate gas tank 1 and $CO_2$ pump 4. Accordingly, pump inlet valve 2 can control the flow of gas from gas tank 1.

$CO_2$ pump 4 functions to provide gas from gas tank 1 to $CO_2$ cleaning vessel 9 as well as to provide the pressures for high-pressure or supercritical fluids. In one aspect, $CO_2$ pump 4 can be calibrated to provide a selected pressure. The $CO_2$ pump 4 is chilled by a water circulator 5 to maintain a low temperature (e.g. 0° C.) to liquefy $CO_2$, in order to provide a high pumping efficiency. Feed valve 8 can control the flow of gas from pump 4 and is located along gas line 2 between the second water circulator 6 and $CO_2$ cleaning vessel 9. The second water circulator 6 raises the $CO_2$ temperature to the desired cleaning temperature. The second water circulator 6 also provide temperature control for the cleaning vessel through the heat-exchange coil 7 inside the cleaning vessel.

The cleaning vessel is equipped with a internal impeller 10, which provides agitation to the $CO_2$ phase and the substrates to be cleaned. Liquid additives 11 are added to the bottom of the cleaning vessel 10. The additives 11 will dissolve into the $CO_2$ phase and form microemulstions which solubilize allergens and endotoxin and remove them from the cleaning substrates. The pressure inside the cleaning vessel is monitored by a pressure gauge 12. Safety head 13 is connected to prevent over pressurization of the cleaning vessel 9. Vent valve 14 is used to release the $CO_2$ pressure inside the cleaning vessel at the end of a cleaning operation.

Example of Endotoxin Solubilization and Removal

Materials:

E. coli 055:B5 endotoxin and *limulus amebocyte* lysate (LAL) kinetic-QCL assay kit were purchased from Lonza Walkersville Inc. (Walkersville, Md.). HyPure™ cell culture grade water (endotoxin-free water) was purchased from HyClone Laboratories Inc. (Logan, Utah). Dehypon Ls-54 surfactant was a gift from Cognis Corporation (Ambler, Pa.).

Quantifying Endotoxin

The level of endotoxin was quantified with a standard LAL assay. Endotoxin catalyze the conversion of a proenzyme in LAL to its enzymatic form. This enzyme is capable of decompose a colorless substrate Ac-LLE-Glu-Ala-Arg-pNA to p-nitroaniline (pNA) which absorbs light at 405 nm. The rate of the color change cause by the production of pNA is used to quantify the endotoxin level.

Procedure

Titanium discs (12 mm diameter, 2.5 mm thickness) were used in the example to demonstrate the effectiveness of the disclosed endotoxin cleaning process. Each disc was coated with approximately 2000 unites of endotoxin (~0.2 microgram of endotoxin). Four discs (three coated, one clean) were glued to the impeller, facing downward. Twelve grams of water and 32 grams of LS-54 surfactant were added to the bottom of the cleaning vessel. After the cleaning vessel was closed, a $CO_2$ pump started to pressurize the vessel with $CO_2$ until reaching the predetermined pressure (2000 or 4000 psi in this example). The temperature was held at constant temperature (5° C. or 40° C. in this example). The impeller was turned on (400 rpm) to provide agitation, in order to facilitate the formation of water-in-$CO_2$ microemulsions and the solubilization of endotoxin into the microemulsion.

The temperature, pressure, and agitation were maintained for the predetermined amount of time. Then the feed valve was closed. The cleaning vessel was slowly depressurized through the vent valve until the vessel reached atmospheric pressure. The impeller was immediately removed from the cleaning vessel. All attached discs were retrieved to determine the remaining endotoxin level with LAL assay.

Results and Discussion

Various combinations of temperature, pressure and processing time have been tested, as summarized in Table 1:

TABLE 1

| Cleaning Fluid (s) | T (C.) | P (psi) | Time (hr) | Initial loading (EU/disk) |
|---|---|---|---|---|
| Supercritical (SC) $CO_2$ | 40 | 4000 | 4 | 2628 |
| $scCO_2$ + Ls-54 & water | 40 | 4000 | 4 | 2628 |
| liquid $CO_2$ | 5 | 4000 | 4 | 2428 ± 71 |
| liquid $CO_2$ + Ls-54 & water | 5 | 4000 | 4 | 2370 ± 82 |
| liquid $CO_2$ + Ls-54 | 5 | 4000 | 4 | 3023 ± 457 |
| liquid $CO_2$ + water | 5 | 4000 | 4 | 2627 ± 265 |
| liquid $CO_2$ + Ls-54 & water | 5 | 2000 | 4 | 2169 ± 810 |
| liquid $CO_2$ + Ls-54 & water | 5 | 4000 | 2 | 3145 ± 438 |

Error! Reference source not found. shows the percentage of endotoxin at different testing conditions. High levels of endotoxin removal have been achieved by adding Ls-54 and water to both supercritical (SC) $CO_2$ (81%) and liquid $CO_2$ (93%). Liquid $CO_2$+Ls-54 and water removed a greater fraction of endotoxin than sc $CO_2$+Ls 54 and water, because Ls-54 has higher solubility in compressed $CO_2$ at lower temperatures and constant pressures.

Figure 5:
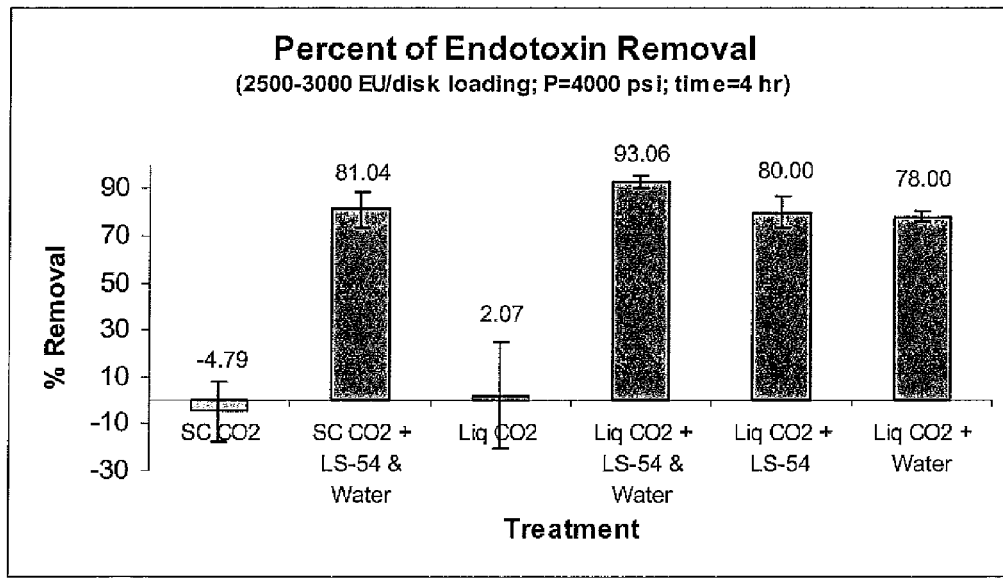
FIG. 5 shows a chart of endotoxin removal with $CO_2$ (liquid and supercritical) and mixtures of water and surfactant Ls-54.
Figure 6:
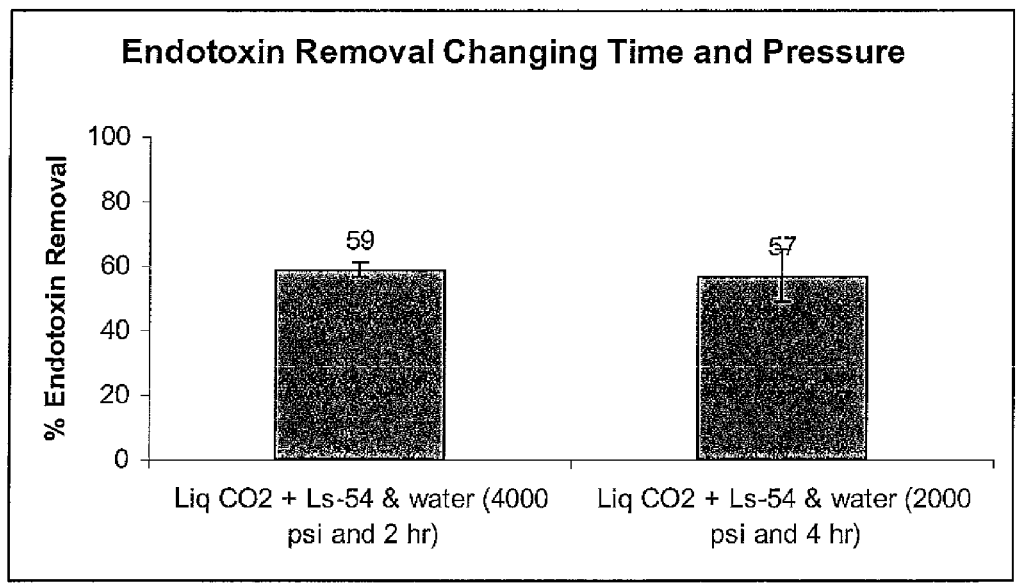
FIG. 6 shows a chart of endotoxin removal for disks treated with liquid $CO_2$+Ls-54 and water at 4,000 psi & 2 hr; and 2,000 psi & 4 hr in the 1 L pressure vessel.

The results indicate that LS-54 microemulsions were formed in $CO_2$ phase and the water in the microemulsions was able to remove significant amount (up to 93%) of endotoxin. (See FIGS. 5 and 6). The higher efficiency achieved in the liquid state (ρ=23.390 mole/L) indicates that more microemulsions are formed in this state than in the supercritical (ρ=20.376 mole/L). Neither $seCO_2$ nor liquid $CO_2$ removed a significant fraction of endotoxin from the Ti surfaces, because $CO_2$ does not dissolve endotoxin.

It was also desired to verify the impact of liquid $CO_2$+Ls-54 and water in removing endotoxin from the metal surfaces decreasing either the time for treatment or the pressure set before (4 hr and 4,000 psi). Error! Reference source not found. shows the results for this set of experiments in terms of percent removal. The average endotoxin level after 2 hour treatment and 4,000 psi was 1296+189 EU/disk with a percent removal of 59±2.4%. For 4 hour treatment and 2,000 psi the average endotoxin remaining was 1004±653 EU/disk with an average percent removal of 57±8%.

Both treatments achieved the same efficacy. However, none of them achieved the efficacy obtained for the 4 hour treatment and 4000 psi (93%). It is noticeable that decreasing either the time or the pressure for treatment will decrease the endotoxin removal in this system. However, it needs to be pointed out that for this system a well-mixed solution for the cleaning fluids is not expected since stirring is not provided.

The shaft holding the disks is allowed to spin within the solution, but complete mixing of the fluids and agitation forces is not guaranteed.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of making a treatment composition, the method comprising:
    loading a substrate into a high pressure vessel;
    loading active components into the high pressure vessel, wherein the active components comprise a protein denaturant and a surfactant; and
    thereafter, pressurizing the high pressure vessel with carbon dioxide to reach a pressure within the high pressure vessel of about 400 pounds per square inch to about 1,070 pounds per square inch.

2. The method as in claim 1, wherein the active components further comprise an acaricide.

3. The method as in claim 2, wherein the acaricide comprises permethrin, benzyl benzoate, or a mixture thereof.

4. The method as in claim 1, wherein the protein denaturant comprises ethanol, hydrogen peroxide, benzyl benzoate, tannic acid, or a mixture thereof.

5. The method as in claim 1, wherein the surfactant comprises a fluorosurfactant, an ionic surfactant, a silicon-based surfactant, a hydrocarbon surfactant, or a mixture thereof.

6. The method as in claim 1, wherein the carbon dioxide has a purity of about 90% by volume or more.

7. The method as in claim 1, wherein the carbon dioxide loaded into the high pressure vessel is substantially pure carbon dioxide gas.

* * * * *